United States Patent [19]

Sinnreich

[11] Patent Number: 4,996,058
[45] Date of Patent: Feb. 26, 1991

[54] COVERED RETARD FORMS

[75] Inventor: Joel Sinnreich, Basel, Switzerland

[73] Assignee: Ciba-Geigy Corporation, Ardsley, N.Y.

[21] Appl. No.: 242,833

[22] Filed: Sep. 12, 1988

[30] Foreign Application Priority Data

Sep. 18, 1987 [CH] Switzerland .................. 3621/87

[51] Int. Cl.$^5$ .............................................. A61K 9/58
[52] U.S. Cl. .................................................. 424/462
[58] Field of Search ......................................... 424/462

[56] References Cited

U.S. PATENT DOCUMENTS

| | | | |
|---|---|---|---|
| 3,901,232 | 8/1975 | Michaels et al. | 128/260 |
| 4,083,951 | 4/1978 | Goudie et al. | 424/44 |
| 4,207,890 | 6/1980 | Mamajek et al. | 128/223 |
| 4,235,236 | 11/1980 | Theeuwes | 128/260 |
| 4,702,918 | 10/1987 | Ushimaru et al. | 424/461 |

FOREIGN PATENT DOCUMENTS 147780 10/1985 European Pat. Off. .
2144051 2/1985 United Kingdom .

Primary Examiner—Merrell C. Cashion, Jr.
Assistant Examiner—Leon R. Horne
Attorney, Agent, or Firm—JoAnn Villamizar

[57] ABSTRACT

The invention relates to a covered, solid retard form which in the case of oral administration remains in the stomach during periodic emptying and ensures continuous release. This dosage form contains the following components:

(a) at least one component that expands on contact with body fluid and that contains a physiologically active substance or a combination of such substances, (b) at least one permeable hydrophilic membrane which surrounds component (a) and which is expansible at the site of use, and optionally (c) a covering which surrounds components (a) and membrane (b) and which disintegrates without delay under the action of a body fluid at the site of use.

5 Claims, No Drawings

COVERED RETARD FORMS

The present invention relates to a covered retard form, to the use of this retard form in therapeutic treatment and to a process for the manufacture of this retard form.

A number of active ingredients that are administered in customary oral dosage forms, such as tablets or capsules, and that are released in the stomach within a short period of time as a result of the rapid disintegration of these dosage forms have an unsatisfactory absorption behaviour. The largest portion of the dosage form is transported into regions of the gastro-intestinal tract having absorption ability, especially in the duodenum and adjoining regions of the small intestine. In the case of water-soluble active ingredients there is a risk of excessive amounts being absorbed rapidly in the duodenum, with undesirable side-effects. In the case of active ingredients having low solubility in water, only small amounts are absorbed, and undissolved portions are transported further into regions of the gastro-intestinal tract having less satisfactory absorption potential. Oral dosage forms having delayed, continuous and controlled release in the region of the stomach therefore have various advantages:

1. The number of administrations can generally be reduced.
2. Effective active ingredient concentrations can be maintained at a uniformly high therapeutic level over a long period, so that any undesirable side-effects that may occur as a result of a too high initial dose at the beginning of administration are reduced and the therapeutic effect is more likely to occur.

U.S. Pat. No. 3 901 232 discloses capsules which, after dissolution in the stomach, liberate a release device for the active ingredient. This release device is attached to a balloon-shaped dilation member which contains a propellant that is vaporisable at body temperature, for example diethyl ether, methyl formate, neopentane etc.. Through the vaporisation of the propellant, the dilation member is filled with gas, floats on the stomach contents and prevents the release device attached to the dilation member from leaving the stomach via the pylorus during the normal emptying process. The active ingredient can be released in a controlled manner, for example from the matrix-like material of the release device.

This dosage form is disadvantageous from the outset because of the propellant used, which is unsuitable for pharmaceutical purposes or even toxic, for example methyl formate. Furthermore, its manufacture is technically complex because of the complicated arrangement of the components.

German Offenlegungsschrift (DE-A) No. 3 527 852 discloses fat-containing pharmaceutical preparations which, as a phase of relatively low specific gravity, float on the gastric juice and effect retarded release of the active ingredient.

It is known that fats, after being absorbed in the stomach, depress peristalsis, so that as a result of the proportion of fats in this formulation, especially saturated fats, the periodic emptying of the stomach is delayed, a smaller amount of the stomach contents is transported further and thus the absorption time is somewhat increased. However, any relatively large ingestion of food breaks up the coherent buoyant fat-containing phase to such an extent that the pylorus can no longer prevent large amounts of this broken-down phase from leaving the stomach. The absorption in the duodenum remains insufficient as a result of this rapid further transport.

The problem underlying the present invention is to produce an improved dosage form having delayed and controlled release. In the case of oral administration, the dosage form should remain in the stomach, despite periodic emptying processes, for more than 4 hours, and preferably for more than 24 hours, and should continue to ensure continuous release even when there is a subsequent ingestion of food. The retard form according to the invention is characterised by (a) at least one component that expands on contact with body fluid and that contains a substance that generates a blowing agent, a physiologically active substance or a combination of physiologically active substances, and optionally a pharmaceutically acceptable hydrophilic swelling agent and further pharmaceutically acceptable adjuncts, (b) at least one hydrophilic membrane which surrounds component (a) and which is expansible at the site of use and is permeable to body fluid, and optionally (c) a covering which surrounds component (a) and membrane (b) and which disintegrates without delay under the action of body fluid at the site of use.

The terms and general definitions used hereinbefore and hereinafter preferably have the following meanings within the framework of the description of the present invention:

The term "retard form" denotes dosage forms which effect delayed release of the active ingredient in comparison with conventional dosage forms, such as customary tablets or capsules, while avoiding an undesirably high initial dose, the release being effected continuously over a relatively long period and controlled at a therapeutically effective level.

In general, retard forms have many advantages, which are described in the literature, see R. Voigt, Lehrbuch der Pharmazeutischen Chemie, Verlag Chemie Weinheim, pp 679 ff.. For example, side-effects are better avoided and the therapeutic index is increased. Furthermore, the active ingredient is better utilised, so that the dose to be administered and/or the number of administrations can be reduced. Retard forms are known for various modes of administration, for example transdermal, intramuscular or oral.

The retard form according to the invention can be used as a therapeutic administration system having valuable pharmacological properties in human and veterinary medicine, not only therapeutically but also prophylactically within the range of indications assigned to a particular active ingredient at the prescribed maximum dosage. The retard form according to the invention is suitable for various modes of administration, oral administration being preferred. It is also suitable, however, for the administration of active ingredients in other cavities in the body, for example in the uterus or in the bladder.

In the retard form according to the invention, component (a), which expands on contact with body fluid, for example gastric juice, contains a substance which, after, for example, oral administration of the retard form, generates the blowing agent itself, for example carbon dioxide, under the action of the body fluid, such as gastric juice, and the hydrogen ions present therein. The expanding membrane (b), which surrounds component (a), is formed as a water-permeable, but to a greater or lesser extent gas-impermeable, sachet which contains component (a) with the substance generating the blowing agent, for example sodium hydrogen carbonate, and the active ingredient. As a result of the evolution of the blowing agent, this sachet inflates and has an increased volume for up to 24 hours. This gas-filled "bag" is able to float on the aqueous phase and is thus retained by the pylorus. During its dwell time in the stomach, the active ingredient present in component (a) is released slowly into the surrounding body fluid, preferably by diffusion, through the membrane of the sachet. Since gastric juice is always being transported further, the active ingredient passes continuously and over a prolonged period into the duodenum, where it is absorbed over an extended period. The retard form according to the invention therefore ensures continuous release of the active ingredient in conjunction with uniform absorption. When used in other cavities of the body, for example in the uterus or in the bladder, release over an even longer period can be achieved.

Component (a), which expands on contact with body fluid, such as gastric juice, effects an increase in the volume of the expansible membrane (b). The increase in volume can be effected by the use of suitable blowing agents and, optionally, hydrophilic swelling agents.

Suitable substances that generate blowing agents are, for example, solids that liberate this agent itself, especially carbon dioxide or nitrogen, for example under the action of body fluid or the hydrogen ions present therein. Such substances generating blowing agents are, for example, those capable of releasing carbon dioxide or nitrogen, for example pharmaceutically acceptable mono- and di-basic salts of carbonic acid, for example alkali metal hydrogen carbonates or alkali metal carbonates, alkaline earth metal carbonates or ammonium carbonate or sodium azide.

Such mono- or di-basic salts of carbonic acid are especially sodium hydrogen carbonate or sodium carbonate, potassium carbonate, calcium carbonate, magnesium carbonate or mixtures thereof. In order to increase the evolution of carbon dioxide, there may be added to the mentioned carbonates the acid component customarily used in effervescent mixtures, for example sodium dihydrogen phosphate or disodium hydrogen phosphate, sodium tartrate, sodium ascorbate or sodium citrate. Also suitable are yeasts which are likewise capable of generating carbon dioxide gas. When yeasts, for example baker's yeast, are used, the necessary nutrients, for example glucose, are added to the formulation.

In addition to the afore-mentioned substances generating blowing agents it is also possible for intensifying the action of the blowing agent to use pharmaceutically acceptable hydrophilic swelling agents, for example partially etherified cellulose derivatives, starches, water-soluble, aliphatic or cyclic poly-N-vinylamides, polyvinyl alcohols, polyacrylates, polymethacrylates, polyethylene glycols or mixtures of these auxiliaries.

Hydrophilic, partially etherified cellulose derivatives are, for example, lower alkyl ethers of cellulose having an average degree of molar substitution (MS) of more than 1 and less than 3 and an average degree of polymerisation of approximately 100–5000.

The degree of substitution is a measure of the substitution of the hydroxy groups by lower alkoxy groups per glucose unit. The average degree of molar substitution (MS) is a mean value and indicates the number of lower alkoxy groups per glucose unit in the polymer.

The average degree of polymerisation (DP) is likewise a mean value and indicates the average number of glucose units in the cellulose polymer.

Lower alkyl ethers of cellulose are, for example, cellulose derivatives that are substituted at the hydroxymethyl group (primary hydroxy group) of the glucose unit forming the cellulose chains and optionally at the second and third secondary hydroxy group by $C_1$–$C_4$alkyl groups, especially methyl or ethyl, or by substituted $C_1$–$C_4$alkyl groups, for example 2-hydroxyethyl, 3-hydroxy-n-propyl, carboxymethyl or 2-carboxyethyl.

Suitable lower alkyl ethers of cellulose are especially methylcellulose, ethylcellulose, methylhydroxyethylcellulose, methylhydroxypropylcellulose, ethylhydroxyethylcellulose, hydroxyethylcellulose, hydroxypropylcellulose, carboxymethylcellulose (in salt form, for example sodium salt form) or methylcarboxymethylcellulose (likewise in salt form, for example sodium salt form).

A starch suitable for use as hydrophilic swelling agent is, for example, a mixture of approximately 15–20 % amylose (molar mass approximately 50,000 to 200,000) and 80–85 % amylopectin (molar mass approximately 100,000 to 1,000,000), for example rice, wheat or potato starch, and also starch derivatives, such as partially synthetic amylopectin, for example sodium carboxymethylamylopectin, and alginates of the alginic acid type.

Water-soluble, aliphatic or cyclic poly-N-vinylamides are, for example, poly-N-vinyl-methylacetamide, poly-N-vinylethylacetamide, poly-N-vinylmethylpropionamide, poly-N-vinylethylpropionamide, poly-N-vinylmethylisobutyramide, poly-N-vinyl-2-pyrrolidone, poly-N-vinyl-2-piperidone, poly-N-vinyl-ε-caprolactam, poly-N-vinyl-5-methyl-2-pyrrolidone or poly-N-vinyl-3-methyl-2-pyrrolidone, especially poly-N-vinylpyrrolidone having a mean molar mass of approximately 10,000–360,000, for example the polyvinylpyrrolidone obtainable under the trade mark Kollidon ® (BASF).

Suitable polyvinyl alcohols have a mean molar mass of approximately 15,000 to 250,000 and a degree of hydrolysis of approximately 70–99 %. Preferred polyvinyl alcohols are those having a degree of hydrolysis of approximately 70–88 % (partially hydrolysed polyvinyl alcohol), for example the polyvinyl alcohol obtainable under the trade name Mowiol ® (Hoechst) denoted by MOWIOL 3-83, 4-80, 4-88, 5-88 or 8-88.

Hydrophilic polyacrylates that can be used as swelling agents have a mean molecular weight of approximately $8.6 \times 10^5$ to $1.0 \times 10^6$. The polyacrylic acid chains carry a greater or smaller number of short side chains and so the individual commercial forms differ in this respect, as well as in having different molecular weights. Neutralised (for example with dilute aqueous sodium hydroxide solution) polyacrylic acid derivatives of the commercial form Carbopol ® (Goodrich), for example CARBOPOL 934 P or CARBOPOL 940, are preferred.

Suitable polymethacrylates are likewise swellable and have a mean molecular weight of more than $1.0 \times 10^6$. Preferred commercial forms that can be used are the polymers of methacrylic acid and methacrylic acid esters of the Eudragit ® type, for example EUDRAGIT L or EUDRAGIT S (Röhm GmbH).

Suitable polyethylene glycols have an average molecular weight of approximately 4000 to 6000. Pharmaceutical- quality commercial forms are preferred, for example polyethylene glycol such as Lutrol ® (BASF), Polydiol ®, Polywachs ® (Hüls), Polyglykol ®, Lanogen ® (Hoechst), Carbowax ® (Union Carbide), Plurocol ® (Wyandotte) or Tetronic ® (Kuhlmann).

Suitable hydrophilic swelling agents are also homopolymers, such as polyhydroxyalkyl methacrylate having a molecular weight from 5,000 to 5,000,000, anionic or cationic hydrogels, mixtures of agar and carboxymethylcellulose, swellable agents consisting of methylcellulose in admixture with weakly cross-linked agar, or water-swellable polymers that can be produced by dispersion of a finely particulate copolymer of maleic acid anhydride and styrene, or tragacanth, gelatine or swellable ion exchange resins.

Swellable ion exchangers are, for example, copolymer resins having acidic groups, for example sulfonic acid groups or salt forms thereof based on styrene-divinylbenzene. Such copolymer resins consist of cross-linked styrene polymers which are obtained by copolymerisation of styrene with divinylbenzene as cross-linking agent. Customary derivatisation reactions, for example sulfonation reactions, are used to incorporate acidic groups, such as sulfo groups, into the structure. The preparation and the properties of these resins are known. Reference is made to the article in Ullmanns Enzyklopädie der Technischen Chemie, 4th Edition, Vol. 13, pp 279 ff., and to Kirk-Othmer, Encyclopaedia of Chemical Technology, J. Wiley, Vol. 13, pp 678 ff, and to the numerous literature references cited therein.

Preferred ion exchange resins are those having quaternary ammonium groups or sulfonic acid groups based on styrene- divinylbenzene which are commercially available and are acceptable for use in pharmaceutical formulations, for example resins marketed by the firm Rohm and Haas under the trade mark Amberlite ® IRP-69.

A physiologically active substance present in the expanding component (a), or a combination of physiologically active substances, is especially a pharmaceutical active ingredient or a combination of pharmaceutical active ingredients. Suitable physiologically active substances are also substances essential for maintaining body functions, such as minerals or vitamins and food additives.

Suitable pharmaceutical active ingredients or combinations are readily soluble in aqueous phase, for example gastric juice, or are absorbable in the dissolved state. Active ingredients that are moderately or sparingly soluble in aqueous phase are present in component (a). Preferably they are present in the form of water-soluble, pharmaceutically acceptable salts, for example as hydrobromide, hydrochloride, mesylate, acetate, succinate, lactate, tartrate, fumarate, sulfate or maleate, etc..

Suitable pharmaceutical active ingredients are, for example, anti-inflammatory agents, for example indomethacin, acetylsalicylic acid, ketoprofen, ibuprofen, mefenamic acid, dexamethasone, sodium dexamethasone sulfate, hydrocortisone or prednisolone, prostaglandins such as prostaglandin $E_1$, $E_2$ or $E_{2\alpha}$, coronary dilatators, for example nifedipine, isosorbide dinitrate, nitroglycerine, diltiazem, trapidil, dipyridamole or dilazep, peripheral vasodilatators, for example ifenprodil, cinepazet maleate, cyclandelate, cinnarizine or pentoxyphylline, antibiotics, for example ampicillin, amoxycillin, cephalexin, cefradin, cefaclor, erythromycin, bacampicillin, minocycline or chloramphenicol, antiseptics for the urinary tract, for example pipemidic acid or nalidixic acid, anti-ulcerants, for example sulperide, cetraxate or gefarnate, antipyretic agents, for example phenacetin, isopropylantipyrine, acetaminophen or benzydamine, anti-spasmodic agents, for example propantheline, atropine or scopolamine, anti-tussives and anti-asthmatics, for example theophylline, aminophylline, methylephedrine, procatechol, trimethoquinol, codeine, clofedanolol or dextromethorphan, diuretics, for example furosemide or acetazolamide, muscle relaxants, for example chlorophenesin carbamate, tolperisone, eperisone or baclofen, mild tranquilisers, for example oxazolam, diazepam, clotiazepam, medazepam, temazepam or fludiazepam, strong tranquilisers, for example sulpiride, clocapramine or zotepine, β-blockers, for example pindolol, propranolol, carteolol, metoprolol or labetalol, anti-arrhythmics, for example procaine amide, disopyramide, ajmaline or quinidine, anti-gout agents, such as allopurinol, anticoagulants, such as ticlopidine, anti-epileptics, for example phenytoin, valproate or carbamazepine, antihistamines, for example chlorpheniramine, clemastine, mequitazine, alimemazine, cyproheptadine, agents against nausea and vertigo, for example diphenidol, methoclopromide, domperidon or betahistine, blood pressure-reducing agents, for example reserpine, rescinnamine, methyldopa, prazosin, clonidine or budralazine, sympathomimetics, for example dihydroergotamine, isoproterenol or etilefrin, expectorants, for example bromohexine, corbocisteine, L-ethylcysteine or L-methylcysteine, oral anti-diabetics, for example glibenclamide or tolbutamide, cardiovascular agents, for example ubidecarenone or adenosine, antacids, for example sodium hydrogen carbonate or sodium carbonate, potassium carbonate or calcium carbonate, or rehydration salts, for example potassium chloride.

Minerals are, for example, under the heading "bioavailable calcium", physiologically usable calcium compounds or compositions containing calcium or calcium mixtures that can be partly or fully absorbed in the upper gastro-intestinal tract, for example bonemeal, shell lime, pure calcium carbonate, calcium sulfate, calcium gluconate, calcium lactate, calcium phosphate (mono- or poly-basic) and calcium levulinate; under the heading "bioavailable magnesium", physiologically usable magnesium compounds or compositions containing magnesium or magnesium mixtures that can be partly or fully absorbed in the upper gastro-intestinal tract, for example magnesium carbonate, magnesium hydroxide or magnesium oxide, "bioavailable" iron components, for example the customary iron-containing mineral additives usually present in oral formulations, for example iron(II) salts, for example iron(II) sulfate, fumarate, gluconate, succinate, glutamate, lactate, citrate, tartrate, pyrophosphate, choline isocitrate or carbonate, or other mineral additives that are present in customary mineral preparations, for example copper in the form of copper(II) oxide, copper sulfate or copper gluconate, phosphorus in the form of calcium phosphate, or phosphorus present in bonemeal, iodine, for example in the form of sodium or potassium iodide, zinc, for example in the form of zinc chloride, zinc sulfate or zinc oxide, chromium in the form of chromium(III) chloride (very small amounts), molybdenum, for example sodium molybdate, selenium in the form of sodium selenate, and manganese, for example in the form of manganese(II) sulfate or chloride. The last-mentioned metal salts are present in the concentrations customary for "trace elements".

Customary vitamin additives are, for example, vitamin A (for example as acetate or palmitate), vitamin D (for example as cholecalciferol), vitamin $B_1$ (for example as thiamine mononitrate), vitamin $B_2$ (for example as riboflavin), vitamin $B_6$ (for example as pyridoxine hydrochloride), vitamin $B_{12}$ (for example as cyanocobalamin), vitamin C (for example as ascorbic acid or sodium ascorbate), vitamin D, vitamin E (for example as d,l-α-tocopheryl acetate), folic acid or niacin (for example as niacin amide). If required, it is possible to add further vitamins, such as vitamin $K_1$ (for example as phytonadione), biotin and pantothenic acid (for example as calcium pantothenate), which can be present in a dose that corresponds to the U.S. RDA (Recommended Daily Allowance) for these additives or, in the case of vitamin $K_1$, a daily dose of up to 100 mg.

Component (a) can also contain the customary pharmaceutical formulation adjuncts that are used at present for the manufacture of oral dosage forms, such as tablets, pellets, microcapsules or retard systems, such as matrix systems, or oral osmotic systems, for example surface-active substances, for example so-called surfactants, for example anionic surfactants of the alkyl sulfate type, for example sodium, potassium or magnesium n-dodecyl sulfate, n-tetradecyl sulfate, n-hexadecyl sulfate or n-octadecyl sulfate, alkyl ether sulfate, for example sodium, potassium or magnesium n-dodecyloxyethyl sulfate, n-tetradecyloxyethyl sulfate, n-hexadecyloxyethyl sulfate or n-octadecyloxyethyl sulfate, or alkanesulfonate, for example sodium, potassium or magnesium n-dodecanesulfonate, n-tetradecanesulfonate, n-hexadecanesulfonate or n-octadecanesulfonate.

Suitable surfactants are also nonionic surfactants of the fatty acid/polyhydroxy alcohol ester type, such as sorbitan monolaurate, monooleate, monostearate or monopalmitate, sorbitan tristearate or trioleate, polyoxyethylene adducts of fatty acid/polyhydroxy alcohol esters, such as polyoxyethylene sorbitan monolaurate, monooleate, monostearate, monopalmitate, tristearate or trioleate, polyethylene glycol/fatty acid esters, such as polyoxyethylene stearate, polyethylene glycol 400 stearate or polyethylene glycol 2000 stearate, especially ethylene oxide/propylene oxide block copolymers of the Pluronics® (BWC) or Synperonic® (ICI) type, myristates and their condensation products, or ethylene oxide homopolymers having a degree of polymerisation of approximately 2,000 to 100,000, which are known, for example, under the trade name Polyox® (Union Carbide).

Further adjuncts are the customary adjuncts used in the manufacture of tablets, pellets, microcapsules, granulates, matrix systems and oral osmotic systems (OROS), for example binders, glidants, flow agents, dispersants, fillers etc.. For example, customary adjuncts such as gelatine, lactose, saccharose, sorbitol, mannitol or cellulose, especially microcrystalline cellulose, or magnesium stearate can be used in addition to the adjuncts mentioned.

The hydrophilic membrane (b), which is expansible at the site of use and is permeable to body fluid, consists of a plastic or wax-like, pharmaceutically acceptable polymeric material that is only slightly gas-permeable or completely gas-impermeable to the blowing agent. Because of its hydrophilic properties, it can absorb body fluid, such as gastric juice, and can effect retarded and continuous release of controlled amounts of the physiologically active substance by means of diffusion or optionally by the use of osmosis.

Suitable plastic or wax-like polymeric materials are especially hydrophilic foils, for example foils of cellulose ethers, such as methyl- or ethyl-cellulose, hydroxypropylcellulose, methyl- or ethyl-hydroxyethylcellulose, methyl- or ethyl-hydroxypropylcellulose, carboxymethylcellulose, polyvinyl acetate, polyvinylpyrrolidone, polyacrylonitrile, mixtures of polyvinylpyrrolidone with polyvinyl alcohol, resins based on phthalic acid anhydride/polyhydroxy alcohol, urethanes, polyamides, shellac, etc..

Especially preferred are polyvinyl alcohols having a degree of hydrolysis of more than 92 % (fully hydrolysed polyvinyl alcohol), especially more than 97 %, for example MOWIOL of the 98 series, for example MOWIOL 4-98, 10-98, 20-98, 28-99, 56-98 and 66-100.

To these materials it is possible to add further adjuncts, for example plasticisers, which improve the elasticity of the covering, for example glycerine, polyethylene glycol/fatty acid esters, such as polyethylene glycol 400 stearate or polyethylene glycol 2000 stearate, triethyl citrate, diethyl phthalate, diethyl sebacate, etc.. The amount of plasticiser added is approximately from 0.01 to 60 % by weight, based on the total weight of the therapeutic system.

Component (a) and the membrane (b) can be arranged in various ways. In a preferred embodiment, component (a) forms the core of the retard form which expands on contact with body fluid, such as gastric juice. This core can consist of a substance that generates a blowing agent, such as sodium hydrogen carbonate, and a pharmaceutical active ingredient. If the substance generating the blowing agent is itself physiologically active, for example as an antacid, such as sodium hydrogen carbonate, the core can consist exclusively of that substance, in which case the expansible permeable membrane (b) is arranged as the covering of the core.

It is also possible for the core to be surrounded not by one but by several coverings of expansible permeable material. With such a multi-layered arrangement, it is also possible for a formulation of the physiologically active substance, or constituents of the formulation, for example the propellant, such as sodium hydrogen carbonate, to be located between the individual layers. With a multi-layered arrangement it is possible to achieve an even longer dwell time of the dosage form at the site of action, for example in the stomach. In addition, the expansible, permeable membrane (b) may itself contain physiologically active substances.

The retard form according to the invention can be provided with a covering (c) which surrounds component (a) and membrane (b) and disintegrates without delay under the action of body fluid at the site of use and which consists of a film coating or, preferably, a covering in capsule form.

Suitable film coatings delay the release of active ingredient only slightly or not at all. Water-soluble film coatings from approximately 20 μm to approximately 100 μm in thickness are preferred.

Suitable film coating materials are especially hydrophilic cellulose derivatives, such as cellulose ethers, for example methylcellulose, hydroxypropylcellulose or especially hydroxypropylmethylcellulose, mixtures of polyvinylpyrrolidone or of a copolymer of polyvinylpyrrolidone and polyvinyl acetate with hydroxypropylmethylcellulose, mixtures of shellac with hydroxypropylmethylcellulose, polyvinyl acetate or copolymers thereof with polyvinylpyrrolidone, or mixtures of water-soluble cellulose derivatives, such as hydroxypropylmethylcellulose, and water-insoluble ethylcellulose. These coating agents can, if desired, be used in admixture with other adjuncts, such as talc, wetting agents, for example polysorbates (for example to facilitate application), or pigments (for example for identification purposes). Depending upon the solubility of the components, these coatings are applied in aqueous solution or in organic solution (for example solutions of shellac or ethylcellulose in organic solvents). It is also possible to use mixtures of acrylates that are water-insoluble per se, for example the copolymer of ethyl acrylate and methyl methacrylate, which are used in aqueous dispersion, with water-soluble adjuncts, for example lactose, polyvinylpyrrolidone, polyethylene glycol or hydroxypropylmethylcellulose.

Instead of using a film-like coating, the retard forms according to the invention can be provided with a covering in capsule form. Hard gelatine capsules having high water-solubility and/or swellability are preferred. Size 0 dry-fill capsules are preferred.

The retard form according to the invention can be of various shapes and may be, for example, round, oval, oblong, tubular and so on, and may be of various sizes depending upon the amount of filling. In addition, the therapeutic system may be transparent, colourless or coloured in order to impart to the product an individual appearance and the ability to be immediately recognised.

The present invention preferably relates to a covered retard form for oral administration, characterised by (a) a component that expands on contact with gastric juice and contains a substance that generates a blowing agent, and pharmaceutical active ingredients, (b) a hydrophilic membrane in the form of a sachet which surrounds component (a) and which is expansible in the stomach and is permeable to gastric juice, and optionally (c) a covering, in the form of film-coatings or capsules, which surrounds component (a) and membrane (b) and which disintegrates after ingestion under the action of gastric juice.

The present invention relates especially to a covered retard form for oral administration, characterised by (a) a component that expands on contact with gastric juice, consisting of a substance capable of yielding carbon dioxide, and a pharmaceutical active ingredient, (b) a polyvinyl alcohol covering, in the form of a sachet, which is expansible in the stomach and is permeable to gastric juice, optionally mixed with plasticisers, and (c) a covering, surrounding component (a) and membrane (b), in the form of capsules which disintegrates after ingestion under the action of gastric juice.

The covered retard form according to the invention can be produced according to known methods, for example by preparing component (a) from a core that expands on contact with body fluid and contains the physiologically active substance or a combination of such substances, for example by mixing, granulating or compressing a substance capable of generating carbon dioxide, such as sodium hydrogen carbonate, with an active ingredient or an active ingredient combination, surrounding this core of component (a) with an expansible membrane (b), which surrounds component (a) in the form of a covering, and providing the formulation composition so covered optionally with a covering (c), surrounding (a) and (b), which disintegrates rapidly on contact with water. This can be effected, for example, by packing the formulation composition consisting of component (a) and membrane (b) into dry-fill capsules of a suitable size.

In a preferred form of the process the expansible permeable membrane (b) surrounding component (a) is produced first, for example by preparing a homogeneous mixture of polyvinyl alcohol and additives, such as plasticisers, for example glycerine and/or polyethylene glycol 400 stearate, by dissolution in water, which is optionally heated, and evaporation to form layers of suitable thickness, for example 100 μm, or by allowing a solution of polyvinyl alcohol in water (without additives) to evaporate. The layers are cut into strips of a suitable size and the active ingredient formulation consisting of component a) is applied. This can be effected, for example, by filling the still open sachet, which is then closed completely, for example by sealing. The sealed sachets can then be filled into dry-fill capsules.

The film or the foil which is obtainable after evaporation of an aqueous solution of polyvinyl alcohol, especially polyvinyl alcohol having a degree of hydrolysis of more than 97 %, and polyethylene glycol/fatty acid ester, for example polyethylene glycol 400 stearate or polyethylene glycol 2000 stearate, optionally with the addition of plasticisers, such as glycerine, is novel and is likewise a subject of the present invention. It is distinguished by a high degree of extensibility. A film-like residue which can be obtained after evaporation of an aqueous solution containing approximately 40–60 % polyvinyl alcohol, 20–40 % polyethylene glycol stearate and 0–30 % glycerine has particularly advantageous properties. This film is distinguished by particularly good extensibility.

The present Examples illustrate but do not limit the invention. Temperatures are given in degrees Celsius.

EXAMPLE 1

(a) 87.8 g of water, 2.4 g of glycerol and 9.8 g of polyvinyl alcohol (Mowiol ® 28-99, Hoechst) are mixed together, stirred and heated to 95°. After cooling to room temperature, the solution is poured onto a glass plate, a layer of approximately 1 mm thickness being formed. This layer is allowed to dry in the air, and the film-like residue is heated to 100° and allowed to cool overnight to room temperature. A soft, flexible film layer of 100 μm thickness is obtained.

Rectangular strips approximately 3 cm in width and 5 cm in length are cut out from this film layer; the strips are folded once and the long sides are sealed to one another to form a sachet approximately 2 cm in internal width and 2.5 cm in length and open at one side. This sachet is filled with a mixture consisting of 300 mg of sodium hydrogen carbonate and 129 mg of polyethylene glycol 400 monostearate (PEG 400 stearate) and the side that is still open is sealed so that a closed sachet having a release surface area of approximately 8 cm² is obtained.

(b) The sachet is placed at 37° into an aqueous sodium chloride/hydrochloric acid solution (2.0 g of NaCl and 2.92 g of HCl 37 % ad 1 liter water), the original volume of approximately 0.5 ml expanding to 1.5 ml after 30 minutes and to 4.5 ml after 8 hours, then falling to approximately 2.9 ml after about 24 hours.

EXAMPLE 2

Analogously to the process described in Example 1, a film layer approximately 140 μm thick is produced from 48% polyvinyl alcohol (MOWIOL 28-99), 32% PEG 400 stearate and 20% glycerol, and is sealed to form open sachets; the open sachets are filled with 300 mg of sodium hydrogen carbonate and are sealed to form closed sachets On the addition of aqueous sodium chloride/hydrochloric acid solution, an expansion in volume from approximately 0.5 ml to 5.5 ml is observed after 30 minutes, to 7.8 ml after 1 hour and to 8.5 ml after 3 hours. The volume falls to 3.3 ml after 6 hours and to 1.9 ml after 24 hours.

EXAMPLE 3

Analogously to the process described in Example 1, a film layer approximately 100 μm thick is produced from 80% polyvinyl alcohol (MOWIOL 28-99) and 20% glycerol, and is sealed to form square open sachets with sides about 2 cm in length; the open sachets are filled with 150 mg of sodium hydrogen carbonate and 150 ml of cold-water-soluble polyvinyl alcohol (MOWIOL 4-88) and sealed to form closed sachets. On the addition of aqueous sodium chloride/hydrochloric acid solution having the composition given in Example 1 b), an expansion in the volume of the sachet from approximately 0.7 ml to 4.2 ml is observed after 30 minutes and to approximately 5.8 ml after 2 hours. The volume falls to 2.8 ml after 6 hours.

EXAMPLE 4

Analogously to the process described in Example 1, a film layer having the composition given in Example 3 is produced and is sealed to form square open sachets with sides about 2 cm in length; these sachets are filled with 30 mg of sodium hydrogen carbonate and 270 mg of sodium carbonate and are sealed to form closed sachets. On the addition of aqueous sodium chloride/hydrochloric acid solution having the composition given in Example 1 (b), an expansion in volume from approximately 0.6 ml to 3.0 ml is observed after 2 hours and to 4.2 ml after 4 hours. After 24 hours the sachet had a volume of approximately 3.4 ml.

EXAMPLE 5

Analogously to the process described in Example 1, a film layer about 100 μm thick is produced from 80% polyvinyl alcohol (MOWIOL 28-99) and 20% glycerol and is sealed to form square open sachets with sides about 2 cm in length; these sachets are filled with 100 mg of sodium hydrogen carbonate and with a smaller sachet with sides about 1.4 cm in length containing approximately 200 mg of sodium hydrogen carbonate, and are sealed to form a closed sachet. On the addition of aqueous sodium chloride/hydrochloric acid solution having the composition given in Example 1 (b), an expansion in volume from 0.7 ml to the following values is observed:

| t [hrs]  | 0   | 0.5 | 1.0 | 2.0 | 3.0 | 4.0 | 5.0 | 6.0 | 8.0 | 9.0 | 24.0 |
|----------|-----|-----|-----|-----|-----|-----|-----|-----|-----|-----|------|
| vol [ml] | 0.7 | 2.7 | 3.6 | 3.5 | 3.0 | 3.9 | 3.9 | 3.9 | 3.5 | 3.3 | 2.7  |

EXAMPLE 6

(a) Analogously to the process described in Example 1, a film layer about 100 μm thick is produced from 64% polyvinyl alcohol (MOWIOL 28-99), 16% PEG 400 stearate and 20% glycerol and is bonded to form square open sachets with sides about 2 cm in length along the inner seam; these sachets are filled with 75 mg of baclofen (Lioresal ®; Ciba-Geigy) and 300 mg of sodium hydrogen carbonate.

On the addition of aqueous sodium chloride/hydrochloric acid solution having the composition given in Example 1 (b), an expansion in volume from 0.6 ml to the following values is observed:

| t [hrs]  | 0   | 0.67 | 1.0 | 2.0 | 3.0 | 4.0 | 6.0 | 7.0 | 8.0 | 24.0 |
|----------|-----|------|-----|-----|-----|-----|-----|-----|-----|------|
| vol [ml] | 0.6 | 4.5  | 4.2 | 4.7 | 5.9 | 5.0 | 3.5 | 2.8 | 3.5 | 3.2  |

(b) An analogous sachet containing 110 mg of baclofen releases the following amount of active ingredient on the addition of 800 ml of aqueous sodium chloride/hydrochloric acid solution having the composition given in Example 1 (b):

| t [hrs]     | 0 | 1.0 | 2.0 | 3.0  | 4.0  | 6.0  | 7.0  | 8.0  | 24.0 |
|-------------|---|-----|-----|------|------|------|------|------|------|
| amount [mg] | 0 | 4.7 | 7.3 | 12.3 | 20.0 | 63.6 | 71.3 | 77.0 | 96.5 |

EXAMPLE 7

Analogously to the process described in Example 1, a film layer about 100 μm thick is produced from 64% polyvinyl alcohol (MOWIOL 28-99), 16% PEG 400 stearate and 20% glycerol and bonded to form octagonal open sachets about 2.25 cm in diameter; these sachets are filled with 100 mg of sodium hydrogen carbonate, 25 mg of baclofen and with a smaller octagonal sachet having a diameter of about 1.6 cm filled with 200 mg of sodium hydrogen carbonate, 86 mg of PEG 400 stearate and 50 mg of baclofen.

On the addition of aqueous sodium chloride/hydrochloric acid solution having the composition given in Example 1 (b), the volume is observed to expand from 0.7 ml to higher values and the following amounts of active ingredient to be released:

| t [hrs]     | 0   | 1.0 | 2.0 | 3.0 | 4.0 | 6.0 | 7.0 | 8.0  | 24.5 |
|-------------|-----|-----|-----|-----|-----|-----|-----|------|------|
| vol [ml]    | 0.7 | 2.0 | 1.8 | 2.1 | 2.9 | 2.7 | 2.8 | 2.8  | 2.0  |
| amount [mg] | 0   | 1.8 | 2.6 | 3.6 | 5.2 | 7.9 | 9.2 | 10.8 | 19.5 |

EXAMPLE 8

Analogously to the process described in Example 1, a film layer about 100 μm thick is produced from 80% (w/w) polyvinyl alcohol (MOWIOL 28-99) and 20% glycerol and is bonded to form rectangular open sachets with sides about 25 mm in length. The sachet is filled in succession with 300 mg of sodium hydrogen carbonate, 300 mg of anhydrous citric acid and 50 mg of metoprolol without mixing the components together. The sachet is evacuated, sealed along the still open seam and heated for 30 minutes at 90° C. On the addition of aqueous sodium chloride/hydrochloric acid solution having the composition given in Example 1, an initial expansion in volume to 14 ml is observed for 30 minutes.

What is claimed is:

1. A film coated or capsule dosage form which effects delayed release of an active pharmaceutical ingredient in the stomach which comprises:
   (a) at least one component that expands on contact with gastric juice and contains an agent capable of releasing carbon dioxide or nitrogen, a pharmaceutically active ingredient or a combination thereof and, optionally, a pharmaceutically acceptable hydrophilic swelling agent selected from the group consisting of lower alkyl ethers of cellulose, starches, water-soluble aliphatic or cyclic poly-N-vinylamides, polyvinyl alcohols, polyacrylates, polymethacrylates, polyethylene glycols and mixtures thereof and further pharmaceutical formulation adjuncts used for the manufacture of oral dosage forms, (b) at least one hydrophilic membrane in the form of a sachet which contains component (a), is expansible by inflation and floating on the aqueous phase in the stomach and permeable to gastric juice and, (c) a film coating or capsule form which contains components (a) and (b) and which disintegrates without delay in the stomach under the action of gastric juice.

2. A capsule dosage form according to claim 1 wherein:

(a) the component that expands on contact with gastric juice and contains an agent capable of releasing carbon dioxide, a pharmaceutically active ingredient and further pharmaceutical formulation adjuncts used for the manufacture of oral dosage forms, (b) the at least one hydrophilic membrane in the form of a sachet which contains component (a), is expansible by inflation and floating on the aqueous phase in the stomach and permeable to gastric juice and, (c) a the capsule form which contains components (a) and (b) and which disintegrates without delay in the stomach under the action of gastric juice.

3. A capsule dosage form according to claim 1 wherein:

(a) the component that expands on contact with gastric juice and contains an agent capable of releasing carbon dioxide, a pharmaceutically active ingredient and further pharmaceutical formulation adjuncts used for the manufacture of oral dosage forms, the at least one hydrophyllic membrane is (b) a polyvinyl alcohol membrane in the form of a sachet which contains component (a), is expansible by inflation and floating on the aqueous phase in the stomach and is permeable to gastric juice and optionally admixed with plasticizers and, the (c) a capsule form which contains components (a) and (b) and which disintegrates without delay in the stomach under the action of gastric juice.

4. A capsule dosage form according to claim 3 wherein the agent capable of releasing carbon dioxide is sodium hydrogen carbonate.

5. A capsule dosage form according to claim 3 wherein component (a) contains baclofen as pharmaceutically active ingredient.

* * * * *